United States Patent [19]
Rauh

[11] Patent Number: 5,922,183
[45] Date of Patent: Jul. 13, 1999

[54] METAL OXIDE MATRIX BIOSENSORS

[75] Inventor: R. David Rauh, Newton, Mass.

[73] Assignee: EIC Laboratories, Inc., Norwood, Mass.

[21] Appl. No.: 08/880,615

[22] Filed: Jun. 23, 1997

[51] Int. Cl.$^6$ .................................................. G01N 27/26
[52] U.S. Cl. ......................... 204/403; 204/415; 435/817; 435/287.1; 435/289.1
[58] Field of Search ........................... 204/290 F, 290 R, 204/291, 292, 403, 415; 435/817, 287.1, 289.1

[56] References Cited

U.S. PATENT DOCUMENTS

| | | |
|---|---|---|
| 4,115,198 | 9/1978 | Coughlin et al. .......................... 195/63 |
| 4,545,382 | 10/1985 | Higgens et al. . |
| 4,613,422 | 9/1986 | Lauks . |
| 4,677,989 | 7/1987 | Robblee . |
| 4,711,245 | 12/1987 | Higgens et al. . |
| 4,970,145 | 11/1990 | Bennetto et al. . |
| 5,200,334 | 4/1993 | Dunn et al. . |
| 5,231,028 | 7/1993 | Mullen . |
| 5,262,035 | 11/1993 | Gregg et al. . |
| 5,264,092 | 11/1993 | Skotheim et al. . |
| 5,320,735 | 6/1994 | Kato et al. . |
| 5,356,786 | 10/1994 | Heller et al. . |
| 5,378,332 | 1/1995 | Pandey . |
| 5,507,936 | 4/1996 | Hatschek et al. . |

OTHER PUBLICATIONS

Bordi, S. et al., "Iridium/Iridium Oxide Electrode for Potentio–metric Determination of Proton Activity on Hydroorganic Solutions at Sub–Zero Temperatures" in Anal.Chem. 56, 317–319 (1984) No month available.
Grubb, W.T. and King, L.H., "Palladium–Pallium Oxide pH Electrodes" in Anal. Chem. 52, 270–273 (1980) No month available.
Messing, R.A., "Adsorption and Inorganic Bridge Formations," in Meth. Enzymology XLIV:149–167 (1976) No month available.

Guilbault et al., "Use of Enzyme Electrodes in Biomedical Investigations," in *Medical and Biological Applications of Electro–chemical Devices,* John Wiley & Sons, New York, pp. 300–301 (1980) No month available.
Kinoshita, K. and Madou, M., "Electrochemical Measurements on Pt, Ir, and Ti Oxides as pH Probes," J. Electrochem. Soc., 131(5):1089–1094 (1984) No month available.
Cass, A.E.G. et al., "Ferrocene–Medicated Enzyme Electrode for Amperometric Determination of Glucose," Amer.Chem.Soc., 56:667–671 (1984) No month available.
Umana, M. and Waller, J., "Protein–Modified Electrodes. The Glucose Oxidase/Polypyrrole System," Amer.Chem.Soc., 58:2979–2983 No month available.
Suva, R. et al., "All Solid–State Urea Sensor," Proc. 2nd Int. Mtg. on Chemical Sensors, Bourdeaux 542–544 (1986) No month available.
Foulds, N.C. and Lowe, C.R., "Immobilization of Glucose Oxidase in Ferrocene–Modified Pyrrole Polymers," Amer.Chem.Soc., 60(22): 2473–2478 (1988) No month available.

(List continued on next page.)

Primary Examiner—Bruce F. Bell

[57] ABSTRACT

A thin film matrix for biomolecules, suitable for forming electrochemical and biosensors comprising a general class of materials known as hydrous metal oxides which are also conductive or semiconductive of electrons and which have been shown to have excellent stability against dissolution or irreversible reaction in aqueous and nonaqueous solutions. The composites are bifunctional, providing both amperometric and potentiometric (pH) transduction. The thin film composites of the oxides and biological molecules such as enzymes, antibodies, antigens and DNA strands can be used for both amperometric and potentiometric sensing. Hydrous Ir oxide is the preferred matrix embodiment, but conducting or semiconducting oxides, of Ru, Pd, Pt, Zr, Ti and Rh and mixtures thereof have similar features. The hydrous oxides are very stable against oxidation damage.

24 Claims, 7 Drawing Sheets

OTHER PUBLICATIONS

Szucs, A. et al., "On the Adsorption of Glucose Oxidase at a Gold Electrode," J. Electrochem. Soc., 136(12):3748–3755 (1989) No month available.

Tran–Minh, C., Pandey, P.C. & Kumaran, S., "Studies on Acetyl–choline Sensor and its Analytical Application Based on the Inhibition of Cholinesterase," Biosensors & Bioelectronics 5:461–471 (1990) No month available.

Gunaratna, P.C. & Wilson, G.S., "Optimization of Multienzyme Flow Reactors for Determination of Acetylcholine," Anal. Chem., 62: 402–407 (1990) No month available.

Heller, A., "Electrical Connections of Enzyme Redox Centers to Electrodes," J. Phys. Chem., 96:3579–3587 (1992) No month available.

Aston, W.J., "Product Design and Development," Biosensors & Bioelectronics, 7:85–89 (1992) No month available.

Audebert, P. and DeMaille, C., "Electrochemical Probing of the Activity of Glucose Oxidase Embedded Sol–Gel Matrices," Chem. Mater., 5:911–913 (1993) No month available.

Glezer, V. and Lev, O., "Sol–Gel Vanadium Pentaoxide Glucose Biosensor," J. Am. Chem. Soc., 115:2533–2534 (1993) No month available.

Millan, K.M. and Mikkelsen, S.R., "Sequence–Selective Biosensor for DNA Based on Electroactive Hybridization Indicators," Anal. Chem., 65:2317–2323 (1993) No month available.

Dave, B.C. et al., "Sol–Gel Encapsulation Methods for Biosensors," Anal. Chem., 66:1120–1127 (1994) No month available.

Du, G. et al., "Electroanalytical Detection of Glucose Using a Cyanometalate–Modified Electrode: Requirements for the Oxidation of Buried Redox Sites in Glucose Oxidase," Anal.Chem. 68:796–806 (1996) No month available.

Hiller, M. et al., "Amperometric Biosensors Produced by Immobilization of Redox Enzymes at Polythiophene–Modified Electrode Surfaces," Adv. Mater. 8:219–222 (1996) No month available.

Bogdanovskaya, V.A. & Tarasevich, M.R., "Electrochemical biosensors for medicine and ecology," Biosensors and Bioelectronics, 11:853–861 (1996) No month available.

Cho, J–H. et al., "Electrochemical adsorption of glucose oxidase onto polypyrrole film for the construction of a glucose biosensor," Sensors and Actuators B 30:137–141 (1996) No month available.

METAL OXIDE MATRIX BIOSENSORS

This invention was made with Government support under Contract No. DAAL01-97-C-0043 awarded by the U.S. Department of the Army. The Government has certain rights to this invention.

FIELD OF INVENTION

This invention relates to electrochemical sensors which employ biological molecules such as enzymes, antibodies and nucleic acids for detection and to matrices for incorporating these biological molecules onto electrodes.

BACKGROUND OF INVENTION

Certain biological molecules or "biomolecules", such as enzymes, antibodies and nucleic acids, possess reactive recognition properties for other molecular species ("substrates"), giving rise to specific complexation, reaction and product formation. Electrochemical biosensors are a class of sensors in which electrochemistry provides a means of signal transduction, either through detection of products of enzyme reactions or of the concentration of electroactive tags used in competitive binding or sandwich immunoassays. The signal may be due to a change in current or in potential on the electrode ("amperometric" or "potentiometric" detection, respectively). A particularly useful type of electrochemical biosensor is produced when the biomolecule is immobilized onto the electrode surface. Electrodes with immobilized enzymes are widely used in glucose monitoring for insulin maintenance, for example.

A common class of biomolecules used to prepare electrochemical biosensors are the so-called "oxidoreductase" enzymes, of which glucose oxidase (GOx) is an illustrative example. GOx catalyzes the reaction between glucose and $O_2$ to produce gluconolactone and $H_2O_2$. The reaction occurs via the intermediate flavin adenosine dinucleotide oxidation-reduction ("redox") system $FAD/FADH_2$, which is incorporated inside the enzyme's protein envelope. Thus, the full reaction is:

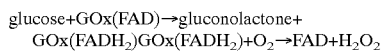
$$glucose + GOx(FAD) \rightarrow gluconolactone + GOx(FADH_2) GOx(FADH_2) + O_2 \rightarrow FAD + H_2O_2$$

If the electrode is maintained at a potential sufficiently positive to oxidize the $H_2O_2$, the current due to $H_2O_2$ oxidation provides a reading of glucose concentration:

$$H_2O_2 \rightarrow 2H^+ + O_2 + 2e^-$$

In amperometric biosensors such as this it is required that the electrochemically active product, be it a freely diffusing product or an electron shuttle contacting the enzyme, efficiently transfer electrons to or from the electrode so that the electrical current can be measured by the external circuit. Enzymes can be immobilized into nonconductive polymer matrices coated onto the surface of electrodes. Such matrices can be made permeable to both substrate and product. However, response may be reduced by the necessity of diffusion of the product through the matrix to the electrode surface. To alleviate this problem, immobilization has been achieved in electrically conductive matrices by numerous means in prior art. For example, matrices composed of platinized, resin bound carbon or graphite particles have been disclosed in U.S. Pat. Nos. 4,970,145 and 5,160,418. Inclusion of Pt oxide in carbon or graphite enzyme electrodes to reduce their activity to alcohols is described in U.S. Pat. No. 5,231,028.

Electrically conductive polymers such as polypyrrole, polyaniline and polythiophene have been demonstrated as encapsulants for oxidoreductase enzymes, see for example M. Trojanowicz et al. (Sensors and Actuators B28, 191–199, 1995) and Hiller et al. Adv. Mater. 8:219–222, 1996) and references cited therein. These conductive or redox polymer matrices serve the dual function of trapping the enzyme and conducting electrons to or from the enzyme, electron transfer mediators or reaction products and the electrode surface. They are also sufficiently porous to provide free transport of electrolyte, substrate and products. Conductive polymer layers containing enzyme may be formed by electropolymerizing the monomer onto the electrode surface in the presence of the enzyme. They may also be formed by biasing a preformed polymer coating in the presence of the enzyme in solution at a positive potential, thus attracting the negatively charged enzyme electrostatically to the polymer matrix.

Conducting polymer encapsulants have several drawbacks that are well known for this class of materials, including poor long-term stability to water, oxygen and temperature, poor stability to products of enzyme reactions (e.g., $H_2O_2$), lack of physical toughness, potential toxicity or instability when implanted into live organisms, poor stability to extremes of electrode polarization and limited pH range. Frequently polymer formation conditions are incompatible with biomolecules, e.g., requiring nonaqueous solvents or extreme pH. In situ electrochemical formation of conductive polymer/biomolecule composites requires compatibility of the biomolecule with monomers such as pyrrole, aniline and thiophene, which is highly uncertain. If the biosensor is to be utilized in vivo, the matrix must be compatible with the physiological environment. This has not been demonstrated for heterocyclic conductive polymers.

Prior art reports on the encapsulation of biological macromolecules at low temperatures and moderate pH in inorganic sol-gel matrices have been promising, both in regard to preserving bioactivity and substrate/product transport and in imparting superior stability against denaturation (see for example U.S. Pat. No. 5,200,334; B. C. Dave et al., Analytical Chemistry 56, 1130A, 1994). Essentially, the matrix forms a water-permeable conforming shell around the molecules, stabilized by ionic interaction, acid-base complexation and hydrogen bonding. Unfortunately this approach has not been readily transferable to coatings for electrodes since the glasses are electrically insulating. One report of trapping of an enzyme in a semiconductive $V_2O_5$ sol-gel glass demonstrated feasibility (V. Glezer and O. Lev, Journal of the American Chemical Society, 115, , see for example 2533, 1993), but the conditions required for formation are generally too aggressive for most biomolecules and $V_2O_5$ has poor long-term stability as an electrode in an aqueous environment.

Prior art has also described means for replacing $O_2$ or other co-factor in oxidoreductase enzymes with an artificial electron acceptor, such as ferricinium U.S. Pat. Nos. 4,545,382, 4,711,245 and 5,378,332. Ferricinium may be generated at the electrode surface by oxidizing ferrocene at <0.2V versus a standard calomel (SCE) reference and will accept an electron from $FADH_2$. Thus, an electrode containing immobilized ferrocene and GOx held at a potential sufficiently positive to generate ferricinium will provide an amperometric response to glucose, but at a lower potential than if $O_2$ were used as the electron acceptor. This approach has been used to produce glucose sensors with reduced susceptibility to oxidizable interferents in blood, such as ascorbate. An additional advantage of ferricinium and similar artificial electron acceptors is that electrode response is independent of $O_2$ tension, which is difficult to control. Some commercial glucose sensors employ glucose oxidase and ferrocene co-immobilized in a carbon matrix. These can only be used once, typically, as the redox mediator will tend to dissolve out of the electrode matrix.

Prior art has also described "wiring" the fast redox couple to the enzyme. Such electrical connection is reviewed by A. Heller (J. Phys. Chem. 92, 3579–3587, 1992). In this approach, the redox couple is covalently immobilized to the matrix or to the protein. For example, matrices comprising polymers with covalently attached redox mediators have been described by Skotheim et al., U.S. Pat. No. 5,264,092. Cross linked polyvinylpyridine complexes of the redox mediator $[Os(bpy)_2Cl]^{+2}$ are described by Gregg and Heller, Analytical Chemistry 62(3), 1990, pp.258–63. Cited advantages of such electrodes include suppression of leaching of the redox mediators by the surrounding solution (implying reusability).

In view of the success of electron transfer mediators, host matrices are also desired which can also incorporate such mediators or which have electron transfer mediators intrinsic to their structure.

Another feature that is increasingly desired in sensors is their ability to be patterned into arrays using thin film photolithographic processing. Composites based on mixing enzymes with carbon or sol-gel precursors can in principle be printed, but structural size and definition are limited. Processes based on electroforming of conductive polymers onto microfabricated metal electrodes are more favorable, but still have the aforementioned problems of polymer matrix stability.

Hydrous metal oxides have been employed as a thin film pH sensing elements for detecting acidic or basic products of enzyme reactions contained in polymeric overlayers, see for example Tranh-Minh, Biosensors and Bioelectronics 5, 461–471 (1990). These overlayers make for electrodes which require several minutes to reach a full response due to diffusional limitations. They also are not readily amenable to high resolution photolithographic patterning.

SUMMARY OF THE INVENTION

It is a general object of this invention to provide a matrix for biomolecules that can be used for their immobilization onto an electrode which is inherently stable in an aqueous environment, including physiological conditions.

It is also an object of this invention to provide a matrix for immobilizing biomolecules that is conductive of electrons and of ions so that it can be used in electrochemical detection and is stable over a wide potential and pH range.

Still another object of this invention is to provide a matrix for immobilizing biomolecules that can be formed in the presence of the biomolecule so as to trap the biomolecule, and that those conditions be conducive to stability of the biomolecule.

Yet another object is to provide a sensor electrode that responds to molecular species recognized by the immobilized biomolecules to give a signal that is proportional to the concentration of said species.

An additional object of this invention is to provide a matrix incorporating redox centers which can transfer an electron directly to/from an active redox center within the immobilized biomolecule.

An additional object is to provide a matrix that protects the enzyme from deactivation over extended storage periods.

Yet another object is to provide a matrix that enables co-immobilization of biomolecules or biomolecules and electron transfer relays in order to provide a multistep reaction environment that can be used as the basis for chemical sensing.

Another object is to provide a conductive matrix for incorporating biomolecules that also exhibits a pH dependent electrochemical potential so that the composite electrode exhibits rapid detection of acidic or basic products of the reactions of said biomolecules with their substrate.

Another object is to provide a matrix for incorporating biomolecules that can be lithographically patterned according to methods familiar to the microelectronics industry.

To achieve the objectives of the present invention, the subject invention is directed to a thin film matrix for biomolecules belonging to a general class of materials known as hydrous metal oxides. A hydrous metal oxide is defined as a metal oxide further incorporating within its structure water of hydration. These materials are typically amorphous and of low density compared to the crystalline parent oxide. They are further characterized by a high degree of porosity with hydroxylated inner surfaces, similar to silica gel. The subject invention deals specifically with the hydrous metal oxides of the noble metals and of Ti and Zr. These are conductive or semiconductive of electrons, and are well known in prior art to have excellent stability against dissolution or irreversible reaction in aqueous and nonaqueous solutions over a wide pH range. They also possess an electrochemical potential that is dependent on pH, see for example Kinoshita and Madou, J. Electrochem Soc 131, 1089–1094 (1984). Thus, these materials are bifunctional in that they can provide both amperometric and potentiometric transduction. Hydrous Ir oxide, which has been patented as a physiological electrode (U.S. Pat. No. 4,677,989) is the preferred matrix embodiment. However conducting or semiconducting oxides derived from metals Ru, Pd, Pt, Zr, Ti and Rh and mixtures thereof have similar features. Thin films range in thickness from a few monolayers (1 nanometer) to approximately 5000 nanometers, but are preferably in the 100 to 1000 nanometer range typical of electrochemically grown oxides.

Composite layers of conducting/semiconducting hydrous metal oxides and biomolecules such as enzymes, cofactors, antibodies, antigens and nucleic acids may be conveniently fabricated by electrochemical means described herein. An electrode of the bare metal, present either in bulk or as a thin film, may be subjected to electrochemical treatments leading to the formation of its native oxide. Surprisingly, if biomolecules are introduced into the formation electrolyte they tend to become concentrated into the oxide layer forming the composite. The subject metal oxides can be formed under mild aqueous and buffered conditions under which biomolecules are stable against hydrolysis and denaturation. No other additives are required that might interact with the biomolecule such as would be required for the formation of a conductive polymer matrix. The porous nature of the oxides also allows their impregnation by biomolecules after they have been formed, such impregnation promoted by dipping the electrode into a solution of the biomolecule or by dropping a solution of the biomolecule onto the oxidized electrode surface, but more effectively by polarizing the oxidized electrode anodically in the presence of the biomolecule. Another means of forming the composites is to electrodeposit the hydrous metal oxide onto a substrate from an electrolyte containing the enzyme and metal ion precursor salts.

Co-immobilization of biomolecules along with incorporation of electron transfer relays is effected by simply forming the oxide in the presence of the entire group of components, by adding the components sequentially during oxide formation, or by dipping or polarizing the electrode in an electrolyte containing the biomolecules or by dropping a solution of the biomolecules onto the electrode surface and allowing the carrying solvent to evaporate.

The composites of the subject hydrous metal oxides and biomolecules can be used as amperometric or potentiometric biosensors for an analyte or substrate of the many varieties described in prior art.

The biomolecules for use in amperometric biosensors are typically oxidoreductase enzymes. Operation of the biosensors at potentials beyond 0.7V versus Ag/AgCl reference electrode or in the presence of $H_2O_2$ is unimpeded by matrix decomposition since the oxides are highly stable under these conditions.

Besides being electrically conductive over a wide range of electrochemical potentials, the subject hydrous metal oxides also exhibit redox reactions related to transformations of the composite metal ions. The sites of these redox reactions can be used as sites of fast electron transfer between the matrix and the biomolecule, second relay or product. Thus, hydrous metal oxides can have a built in electron relay that can facilitate amperometric operation. Such relays can themselves constitute a cofactor for enzyme operation, obviating the requirement for $O_2$ or other cofactors found in the natural environment. Such relays can also provide for sensor operation at potentials which avoid the detection of common electroactive interferents.

Additional electron transfer relays among those demonstrated in prior art may be incorporated into the hydrous metal oxide matrices by ion exchange, electrostatic binding or polymerization. Multiple enzymes may be incorporated into the matrices for sensing multiple analytes, for eliminating interferents, or for promoting sequential reactions on a substrate, finally ending in an oxidizable or reducable product.

Composites of the subject hydrous metal oxides and biomolecules can also be employed as potentiometric biosensors. This is applicable if the enzyme or multienzyme reaction sequence interact with the substrate to produce an acidic or basic end product which changes the oxide's level of protonation/hydroxylation at the inner surfaces. The result will be a change in the electrode potential versus a standard reference electrode. The potential variation is predicted by the Nernst equation as approximately 59 mV/pH unit. An advantage of having a composite of the oxide and the biomolecule is that the reaction site and the acid-base inner surfaces are very close. Thus, a rapid response is obtained. If the acid-base generating enzyme is constrained to a polymer layer on top of the oxide electrode, then products must diffuse into the electrode until equilibration is achieved. This is generally a slow process.

The invention permits biosensors to be integrated into microelectronic structures such as might be implanted into the body. This is a result of the ease of lithographically patterning thin films of the parent metals such as Ir. Arrays of electrodes of the parent metals may be produced on a variety of insulating substrates such as oxidized silicon, glass, alumina or plastics. These may be individually activated in the presence of different enzymes, for examples, thus producing a multianalyte electrode array. These electrodes may be used for the assay of localized concentrations of analytes in the body, since hydrous Ir oxide, at least, is biocompatible.

One means of forming a multienzyme electrode array is to activate the elements of the array sequentially in different electrolytes containing the different biomolecules. Consider for example an array containing five lithographically defined thin film Ir metal electrodes with five individually addressable contacts labeled 1 to 5. First the array would be lowered into the electrolyte containing a first enzyme and the electrode activated. The other electrodes would not be connected or would be biased at a potential disfavorable to the adsorption of the first enzyme. The array would then be rinsed and introduced into a second electrolyte containing a second enzyme. Here the second electrode would be activated while the other elements were floating or polarized to avoid adsorption of the second enzyme. This sequence would be repeated for the other electrode elements in electrolytes containing other enzymes. In this way a multienzyme sensor array is produced.

The above is just one means for producing a multielement biosensor array using a metal oxide matrix. The aforementioned methods of polarizing a preformed oxide sequentially in the different enzyme solutions is also a possible means. Enzyme solutions may also be dropped onto individual array elements and allowed to become immobilized by absorption, similar to well known enzyme immobilizations in porous silica and titania.

Yet another means of forming the composite oxide and enzyme is to electrodeposit the oxide from a precursor solution of metal salts and the enzyme. In this case, the enzyme is incorporated into the oxide as it is formed. An advantage of this approach is that it is readily adapted to non-Ir (or other parent metal) substrates.

The metal oxide may be used alone or in combination with other sensor elements. For example, diffusion membranes may be added to the electrode surface to control flow of analyte and to manipulate the electrode's dynamic range. Membranes containing other enzymes that precondition the analyte may be added over a composite electrode containing a second enzyme or enzymes for detection.

DESCRIPTION OF PREFERRED EMBODIMENTS

Figure 1:
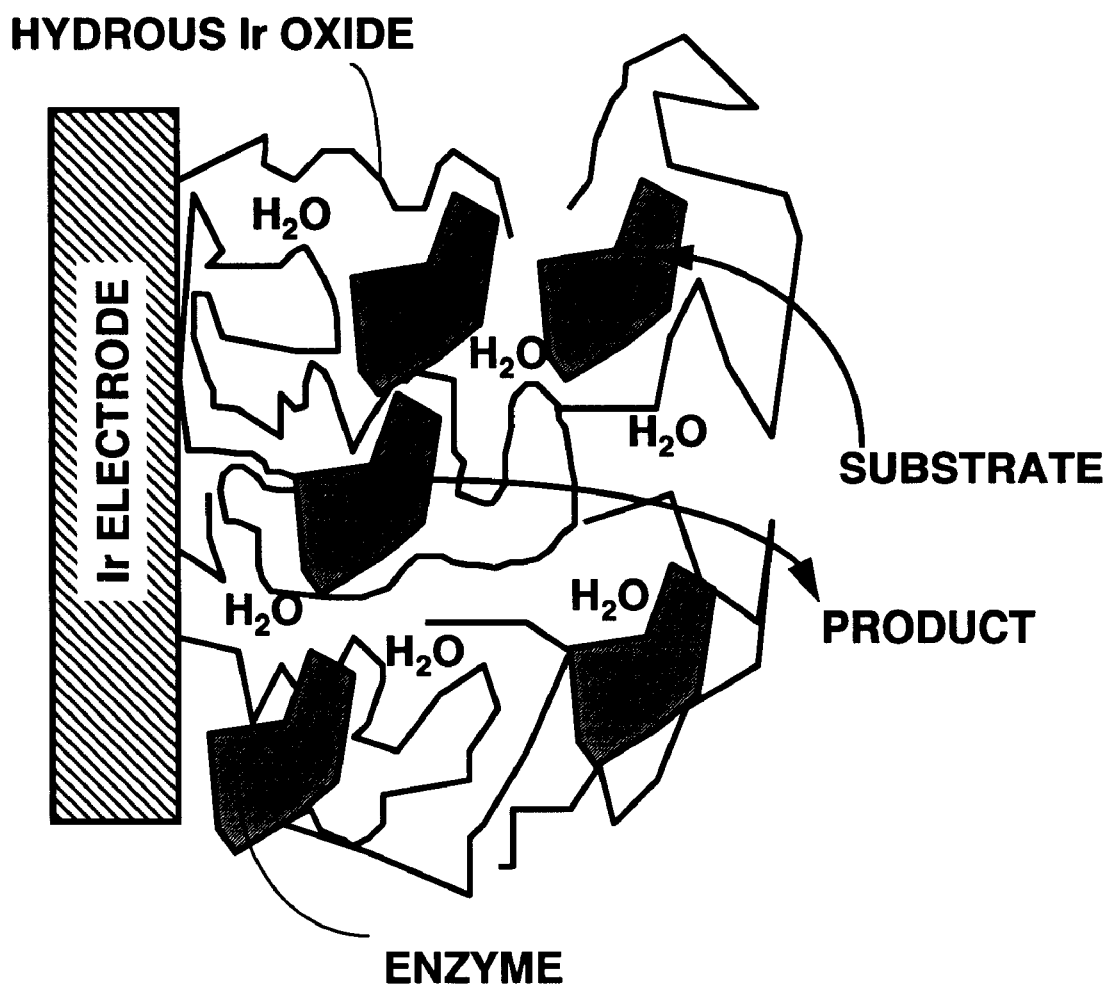
FIG. 1 provides a schematic representation of enzyme entrapment in a hydrous Ir oxide matrix. The matrix is electrically connected to the electrode and connected to the solution by free flow of reactants and products.

The invention is a composite thin film electrode material useful in fabricating electrochemical biosensors. It is composed of a conducting or semiconducting hydrous metal oxide. Disposed in the bulk or on the surface of the oxide is one or more biomolecules and cofactors. The biomolecules react with analytes or substrates to give electroactive products which can be measured electrochemically, either amperometrically or potentiometrically. The metal oxide matrix mediates the electron transfer from these products to the electrode surface and into the external measuring circuit. The hydrous metal oxide is derived substantially from Ir, Ru, Pd, Pt, Zr, Ti and Rh, or mixtures thereof. These oxides are both electrically conductive/semiconductive and stable over a wide range of electrochemical polarizations and pH conditions, including those supportive of biomolecules. The preferred oxide is Ir oxide because it has ideal electronic and morphological properties and because it is readily grown on the native metal under physiological and other biocompatible conditions. It is also a well-known physiological electrode.

Hydrous Ir oxide may be formed by cycling an Ir electrode between positive and negative potential limits in aqueous electrolytes. Electrochemical oxide growth is observed in acid, neutral and basic solutions. Oxide growth is typically monitored by cyclic voltammetry, which reveals an increasing charge capacity during activation. This capacity results from at least a 1 electron Ir ion valence change throughout the bulk of the oxide. The reaction is related to the interconversion of the Ir hydrous oxides with structures tentatively assigned by Burke and Whelan, Journal of Electroanalytical Chemistry v. 162, pp. 121–141 (1984):

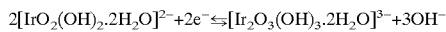

The open circuit potential of the oxide films undergo a pH dependence of ~50–90 mV/pH unit indicative of a dynamic acid-base equilibrium that may include several oxide species. The low density, spongy, amorphous morphology of the films reflects a hydrous structure with hydroxylated inner surfaces. The Ir atoms are connected along some directions by bridging oxygen bonds, while in other directions they are terminated by —O$^-$, OH and OH$_2^+$. This forms a polyoxometallate network with voids shown by transmission electron microscopy to range from 25 Å to 100 Å.

The presence of microvoids throughout the film, observed in published work using transmission electron microscopy (McIntyre et al., Journal of the Electrochemical Society Vol. 127, pp. 1264–1268, 1984), provides a feasible means for inclusion of large biomolecules at all stages of growth, i.e., that the molecules can become adsorbed, then further hydrous oxide can grow around it. This could occur by dissolution/precipitation of the oxide, or by field-assisted diffusion of the macromolecules into the low density hydrous oxide matrix. The mechanism of microvoid formation in Ir oxide has not been determined. In addition, hydrous oxides frequently have a very low density and high internal surface area which can promote molecular incorporation by adsorption or ion exchange.

Oxides of Ir and related metals formed by processes such as anodization, electrodeposition, thermal decomposition of precursor salts, sol gel and vacuum evaporation can be made to exhibit a porous low density morphology by appropriate variation of the conditions of formation. The porosity and hydroxylated inner surfaces of these layers are conducive to enabling large biomolecules to enter into the matrix by adsorption. Adsorption may be further assisted by application of an electrode potential of polarity opposite from the net surface polarity of the biomolecule.

Thin film hydrous, conductive/semiconductive oxides, exemplified by Ir oxide, serve as highly effective and stable matrices for encapsulating enzymes and other biomolecules. The trapped enzyme is shown schematically in FIG. 1. The oxide matrix may be used to oxidize or reduce the primary product of the enzyme-substrate reaction, e.g., H$_2$O$_2$ in the case of the enzyme glucose oxidase (GOx) and many other oxidases. The small molecule product is produced within the protein globule, but then can easily diffuse out. A three dimensional conductive matrix contacting both the electrode and the protein surface provides a means of immediate interception of the oxidizable species.

It is a feature of this invention in this regard that Ir oxide and the other subject oxides provide a highly inert conductive matrix that does not degrade in the presence of oxidizing products like H$_2$O$_2$, a problem noted for conductive polymer matrices employed in prior art. Thus, Ir oxide can be used to encapsulate enzymes that react with the substrate and oxygen to produce an oxidized product and H$_2$O$_2$. These enzymes include oxidases of glucose, hexose, cholesterol, aryl alcohol, gluconolactone, galactose, glycoxylate, lactate, glutamate, pyranose, sorbose, pyridoxine, primary alcohols, catachol, 1,2 hydroxyacids, ecdysone and choline. A more complete listing of oxidoreductase enzymes is to be found in *Enzymes* by M. Dixon et al., 3rd edition, Academic Press, 1979. Thus, sensors for these substrates can be fabricated with the subject oxide/enzyme composites operating at greater than about 0.6V versus Ag/AgCl.

Thus, the following representation of the redox behavior is consistent with the mixed valence hydrous oxide structure, using the Ir oxide example:

1. In reduction, an electron is injected into the oxide network from the electrode.
2. The electron is transported through the polyoxometallate network by a hopping mechanism from Ir$^{+3}$ to Ir$^{+4}$ sites.
3. The electron becomes localized as an Ir$^{+3}$ site.
4. Anions and cations move freely through the porous matrix to compensate the charge, which may also be accompanied by changes in the Ir—O—Ir bonding. A reverse scenario occurs for oxidation. The electrode is highly reversible.

Figure 2:
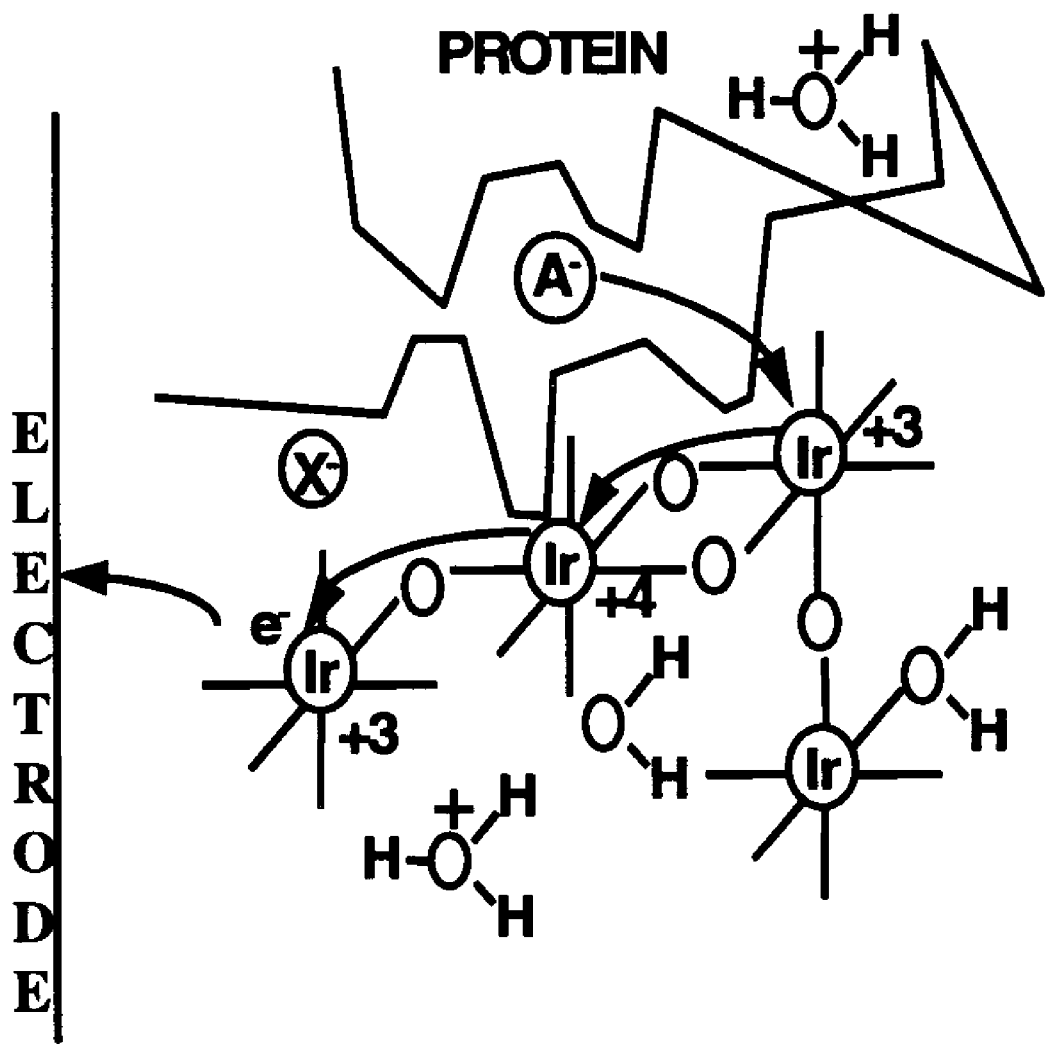
FIG. 2 shows schematically electron transfer from the active enzyme site ($A^-$) to a neighboring $Ir^{+4}$ site and, by hopping conduction through an Ir oxide network, to the electrode.

Note that in the case of Ir oxide, Ir$^{+3}$ or Ir$^{+4}$ sites near to the enzyme active region can act as donors or acceptors, respectively. This is illustrated in FIG. 2. An Ir$^{+4}$ acceptor, which is placed at about 0.2V versus Ag/AgCl in a typical hydrous oxide at neutral pH, can thus under some conditions take the place of O$_2$ or other co-factor in a reaction involving an oxidoreductase enzyme. Thus, in cases where the active site is sufficiently close to the enzyme surface for electron tunneling to occur to the surrounding metal oxide matrix, the oxide also acts as the electron transfer mediator. This transfer is shown in FIG. 2 as an electron transfer from a reduced acceptor, A$^-$, to an Ir$^{+4}$ site. It is well established in prior art that the Ir$^{+3}$/Ir$^{+4}$ redox reactions in Ir oxide films are both rapid and reversible for many cycles in physiological stimulation electrodes, so highly reversible enzyme electrodes are possible.

Co-immobilization of two or more enzymes can be brought about by growing the oxide in contact with the appropriate enzyme mixture. For example, Ir oxide can be grown in a mixture of acetylcholinesterase (AChE) and choline oxidase to sense acetylcholine. In this case, acetylcholine interacts with the esterase to produce choline. The choline then interacts with the oxidase to produce betaine aldehyde and H$_2$O$_2$ when O$_2$ is an acceptor, or another quantifiable reduced species when another co-factor is used. As indicated above, the co-factor can be the matrix itself.

Additional electron transfer mediators can be co-immobilized into the oxide matrix by electrostatic binding. Useful electron transfer shuttles need to be reversible redox moieties. They must further be capable of transferring electrons to or from the active redox site of the oxidoreductase enzyme. Active redox centers within these enzymes are typically FAD/FADH, $NAD^+$/NADH, $NADP^+$/NADPH and porphyrin derivatives. Electron transfer mediators useful for these centers are ferrocenes, quinones, and metal complexes of Ir, Ru and Os. Derivatives of these mediators may be prepared to enhance the ionostatic binding in the metal oxide matrix, for example ferrocene with carboxylate substituents. Similarly, electron transfer shuttle bearing polymers or oligomers can be formed in situ electrochemically in the electrode's porous matrix.

Amperometric sensors based on oxidoreductase enzymes have numerous applications. For example, glucose oxidase electrodes can be used to monitor glucose concentration in the blood of diabetics. Cholinesterase electrodes can be used to assay for acetylcholine activity and inhibition by nerve agents used in chemical warfare or by pesticides. Serum cholesterol can be determined using cholesterol oxidase electrodes. Blood alcohol level is able to be measured by an amperometric response of blood or blood plasma to an alcohol oxidase electrode.

The electrodes may be used in many of the electrochemical biosensor apparatus described in prior art. One preferred arrangement is for the enzyme electrode to be the working electrode member of a three electrode configuration in an electrochemical cell. The cell also contains a counter electrode and a reference electrode such as saturated calomel or Ag/AgCl. In one mode of operation the working electrode is held at a fixed potential versus the reference using a potentiostat. A sample containing the analyte is added to the electrolyte and a current is registered in the external circuit that is proportional to the analyte concentration. In order for this current to be measured, the potential must be fixed at a value sufficient to oxidize (or reduce) the electroactive product of the enzyme-substrate reaction.

The enzyme can also be provided in a two electrode configuration in which the second electrode is both the counter and the reference electrode. Such a configuration is convenient for analysis of a drop of solution, such as blood, which may be placed to bridge two electrodes, as in glucose test strips for blood glucose monitoring.

The metal oxides also function as pH electrodes with their open circuit potentials varying monotonically with pH. Enzymes which give products that alter the pH of the local environment may also be trapped within the oxide matrix. The potential of the electrode may then be calibrated as a function of substrate concentration, providing a potentiometric enzyme electrode. Enzymes reacting with substrate to yield acidic or basic products that are suitable for potentiometric analysis include acetylcholinesterase, butyrylcholinesterase, uricase, urease, penicillinase, adenosine deaminase and methionine lyase. A more complete listing of such enzymes is to be found in *Enzymes* by M. Dixon et al., 3rd edition, Academic Press, 1979.

In principle, the hydrous oxides can be used to immobilize any biomolecule in the hydrous metal oxide, such as antibodies. An immobilized antibody will attract an antigen in solution forming a strongly bound complex. In one scheme, a "sandwich assay", the antibody is exposed to a solution containing an unknown concentration of an antigen, thus blocking some fraction of the antibody binding sites. Next the electrode is exposed to a solution of the antibody that binds specifically to the antibody-antigen complex and which is labeled with an electroactive group such as an oxidoreductase enzyme. The surface concentration of the labeled complex may then be read out amperometrically or potentiometrically by exposing the electrode to a solution of the substrate specific to the label, e.g., glucose in the case of a GOx label. Other schemes for electrochemical immunosensing are possible, for example allowing labeled antigen to compete for binding sites with the unlabeled antigen of unknown concentration ("competitive binding immunoassay").

Immobilizing enzyme substrates in the hydrous metal oxide matrix is also possible. Thus, an electrode for detecting the concentration or activity of an enzyme in solution may be made by interaction with the electrode-bound substrate to form a detectable product (amperometric or potentiometric). For example, a potentiometric sensor for acetylcholinesterase activity in blood may be made using a hydrous metal oxide electrode impregnated with a acetylcholine. The amount of acetic acid formed, and thus the potentiometric response, will be a function of the amount of active enzyme in the blood analyte solution.

Nucleic acid strands may also be immobilized onto the oxides, thus forming highly specific recognition sites for strands of complementary bases. When electrochemically active labels are used to detect the double strands such sensors may be used in DNA-based diagnostics.

The following specific examples illustrate how the invention may be exercised but should not be construed to limit the scope of the invention as delineated in the claims.

EXAMPLE 1

Glucose oxidase/Ir oxide electrode for determining glucose. A three electrode electrochemical cell with 10 ml of electrolyte was employed for oxide growth and for sensor measurements. A 1 mm diameter Ir wire encapsulated in epoxy and polished flat was used as the working electrode. A Bioanalytical Systems Ag/AgCl single junction reference electrode and a 2 $cm^2$ Pt flag counter electrode were also employed. Potential control was achieved with a Solartron SI 1287 Electrochemical Interface and associated data acquisition and control software. Oxide growth was carried out in 0.1M phosphate buffered saline (PBS, pH 7.2) by pulsing between $-0.6$ V and 0.8 V at 1 Hz for 800 cycles. This procedure provides a layer with a charge capacity of 30–35 millicoulombs/$cm^2$. Enzyme incorporation into the electrode was achieved by dissolving the enzyme into the electrolyte immediately before activation. After activation and impregnation, electrodes were rinsed several times with distilled deionized water and stored at 4° C. in 0.1M PBS.

Figure 3:
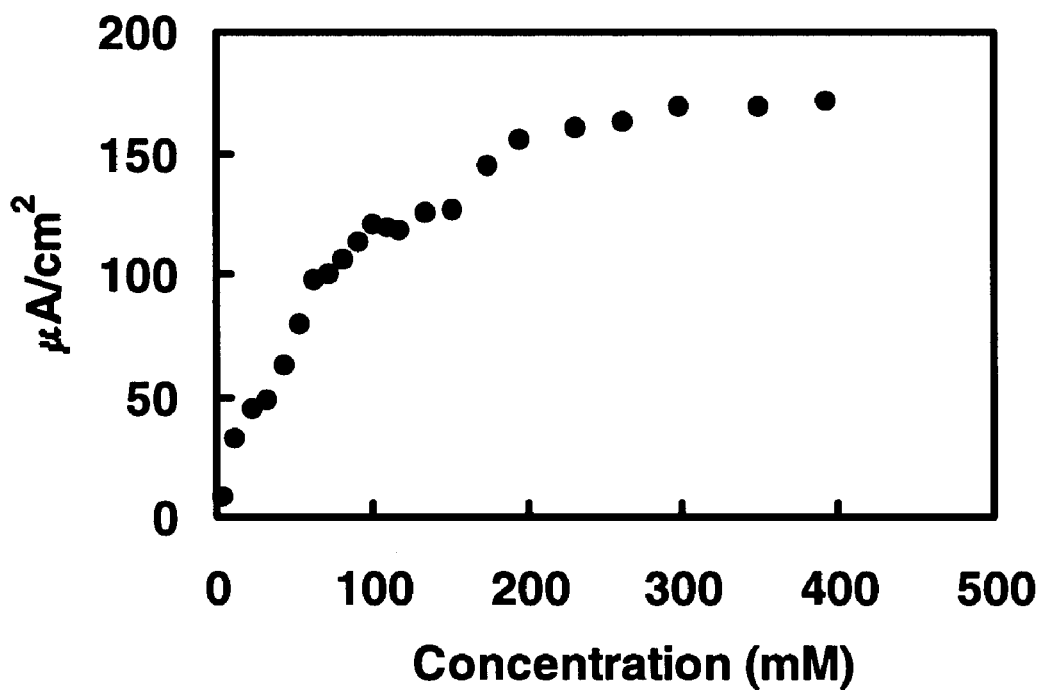
FIG. 3 shows the response of an Ir oxide electrode anodically formed in the presence of GOx to added concentrations of glucose.

Glucose oxidase (Sigma, 15–25 U/mg solid) was dissolved to the level of 1000 U/ml in 0.1M PBS and the electrode activated according to the above protocol. Amperometric measurements of electrode activity were conducted in 0.1M PBS which had been purged for 10 minutes with Ar. The electrode was maintained at the measurement potential, typically 0.7V versus Ag/AgCl in these studies, and the electrode's capacitative current allowed to decay to $<1$ $\mu A/cm^2$. The analyte was then added incrementally and the steady state current measured after each addition. As shown in FIG. 3, this electrode responded with a calibration curve that increases at low substrate concentration, then levels off to a saturation value. This behavior can be described with simple Michaelis-Menton enzyme kinetics and is typical of GOx enzyme electrodes. The dynamic range for the electrode and the saturation current densities obtained (180–200 $\mu A/cm^2$) are large compared to many other GOx electrodes reported in prior art. This is a direct result of the uniquely high surface area Ir oxide morphology. The closest analogy to the present system is the use of conductive polymers to entrap GOx, e.g., polypyrrole. A report by Cho et al. (Sensors and Actuators B 30, 137 (1996)) on GOx/polypyrrole electrodes formed by electroadsorption of GOx into the preformed polypyrrole matrix exhibited a saturation current of 11 $\mu A/cm^2$ at 100 mM glucose, 0.7V polarization.

Since $O_2$ was removed from the electrolyte, the results in this example indicate that reduced $FADH_2$ in the enzyme is transferring its electron directly to the metal oxide matrix. Direct transfer between adsorbed $GOx(FADH_2)$ and an electrode surface has been observed in prior art (Lin and Bocarsley (1996), Anal. Chem. 68: 796–806). If the electrolyte is purged with $O_2$, then $H_2O_2$ is formed as the end product, which can also be detected amperometrically by the Ir oxide matrix electrode.

Electrodes impregnated with GOx were stored in 0.1M PBS at room temperature. These conditions are more extreme than the usual storage conditions of 4° C. frequently reported in the prior art for GOx electrodes. Before each measurement a blank was recorded to establish any residual background current. Responses were then measured to 100 mM glucose. In the electrode tested there was an initial decline in activity over the first 14 days, followed by some regaining of response. After one month of storage the electrodes are still active but only with about 20% of the fresh electrode response. Nevertheless, the current densities of the aged electrodes are close to or exceed those reported for many GOx electrodes in prior art. An interpretation is that some of the GOx is buried deeper in the Ir oxide matrix and is more protected. Also, there is some evolution of the oxide morphology which may enhance the access of the enzyme by glucose.

TABLE 1

Storage of GOx impregnated Ir oxide electrode in 0.1 M phosphate buffered saline (PBS) at room temperature. Response to 90.9 mM glucose at 0.7 V. Electrode area = 7.85 × 10$^{-3}$ cm$^2$

| Days | nA |
|---|---|
| 0 | 190 |
| 1 | 60 |
| 2 | 48 |
| 3 | 35 |
| 9 | 32 |
| 10 | 34 |
| 14 | 12 |
| 16 | 19 |
| 21 | 47 |
| 23 | 37 |

Table 2 presents several electrode loading procedures for preparing GOx-impregnated electrodes. Activities of each different electrode were measured in Ar-purged solutions by polarizing the electrode at 0.7V in 0.1N PBS electrolyte, allowing the capacitative current associated with the porous electrode structure to minimize, then adding glucose to 100 mM. The responses for the different preparations in Table 2 are summarized in Table 3. Responses to glucose in the absence of enzyme were negligible. All protocols in Table 2 produced enzyme-active electrodes. The most active electrodes were produced by growing the oxide in the presence of the GOx.

TABLE 2

Protocols for incorporating enzymes into Ir oxide electrodes.

| Scheme | Procedure |
|---|---|
| A | Activate electrode in a solution containing the enzyme. |
| P | Polarize the activated electrode at 0.7 V for 20 minutes in an electrolyte containing the enzyme to permit anodic adsorption of the negatively charged enzyme. |
| C | Cycle the activated electrode in an electrolyte containing the enzyme between –0.6 V and 0.8 V versus Ag/AgCl reference. |
| W | Wet the dried, activated electrode with an enzyme solution and allow water to evaporate. Rinse electrode with distilled $H_2O$. |
| D | Dip the activated electrode in an enzyme solution for 10 minutes, then rinse with distilled $H_2O$. |
| E | Electrodeposit Ir oxide in solution containing enzyme. |

TABLE 3

Results for limiting response of several oxidase electrodes (1 mm diameter disks) prepared by trapping the enzyme in an anodic iridium oxide matrix. The background current is given as $i_0$ and the current density above background is given as $\Delta i_{sat}$. All measurements made at 0.7 V. Solutions purged for 15 min in Ar before measurements.

| Adsorption Protocol | Charge Capacity (mC/cm$^2$) | [GOx] U/ml | $i_0$, $\mu A/cm^2$ | $\Delta i_{sat}$, $\mu A/cm^2$ |
|---|---|---|---|---|
| A | 30 | 1000 | 9 | 120 |
| C | 14 | 1000 | 2 | 25 |
| P | 29 | 100 | 1.66 | 6.24 |
| W | 16 | 7116 | 21 | 24.5 |
| D | 35 | 1000 | 5 | 12.1 |
| E | 16.3 | 1000 | 7 | 12.9 |

The experimental evidence indicates that the enzyme GOx becomes trapped in the oxide matrix if the Ir is activated in its presence at pH 7. The enzyme has a 60×52× 77 Å spheroid shape, within the range of the anodic oxide void size. The isoelectric point of GOx is 4.2, so it is negatively charged at pH 7. Ellipsometric investigations in prior art have shown that GOx absorbs at Au electrodes as the potential is swept positive of the metal isoelectric point (~–0V/NHE) (Szucs et al., Journal of the Electrochemical Society 136(12), 1989, pp. 3748–3754). Similarly, the enzyme should be attracted to the positively charged sites at the Ir oxide surface during anodization, enhancing the enzyme loading effect above that which would be expected from simple physical trapping. Proteins are generally negatively charged in neutral aqueous solution. However, the metal oxides can absorb either anions or cations, depending on their direction of polarization.

EXAMPLE 2

Figure 4:
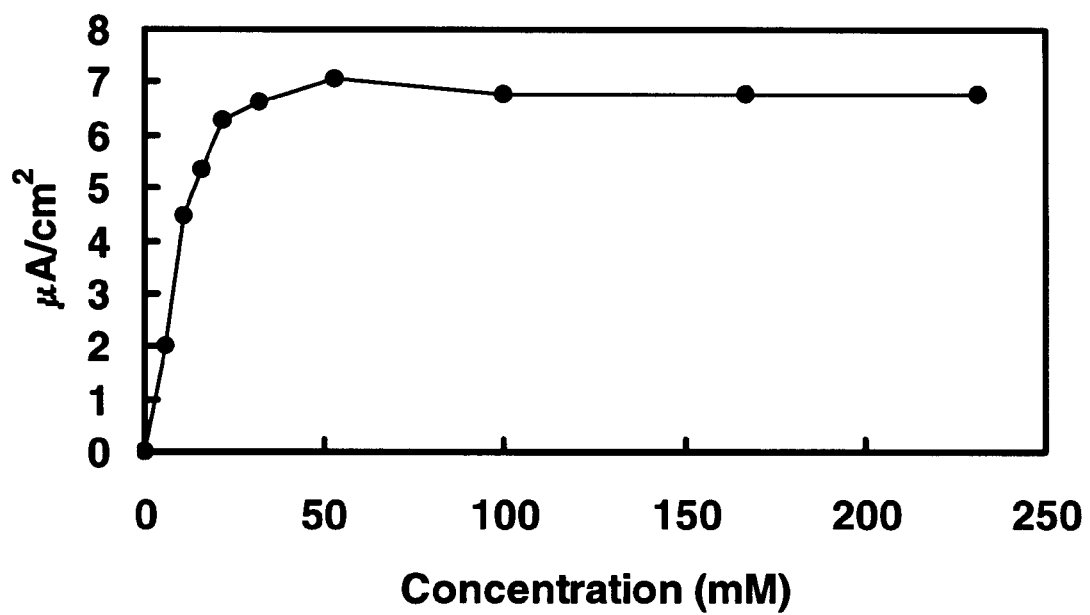
FIG. 4 shows the response of an Ir oxide electrode anodically formed in the presence of choline oxidase and acetylcholinesterase to added concentrations of acetylcholine.

AChE/ChOx electrode for determining acetylcholine. An amperometric electrode sensitive to acetylcholine was fabricated by co-incorporating acetylcholinesterase (AChE) and choline oxidase (ChOx) into anodically formed Ir oxide. The formation electrolyte contained 1000 U/ml and 100 U/ml of the respective enzymes dissolved in 0.1M PBS. Activation proceeded as in Example 1. The amperometric response curve (0.7V) for the activated ChOx/AChE dual enzyme electrode to solution additions of acetylcholine is shown in FIG. 4. Neither enzyme alone gave a responded amperometrically to acetylcholine. Choline oxidase singly immobilized in the electrode gave an amperometric response to choline at this potential. Hence, the dual-enzyme electrode is detecting the internal $FADH_2$ or $H_2O_2$ produced by the choline oxidase catalyzed oxidation of choline derived from the interaction of acetylcholine with AChE:

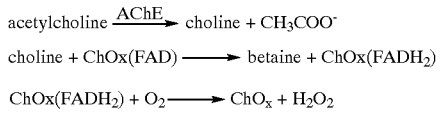

choline + ChOx(FAD) ⟶ betaine + ChOx(FADH$_2$)

ChOx(FADH$_2$) + O$_2$ ⟶ ChO$_x$ + H$_2$O$_2$

EXAMPLE 3

Figure 5:
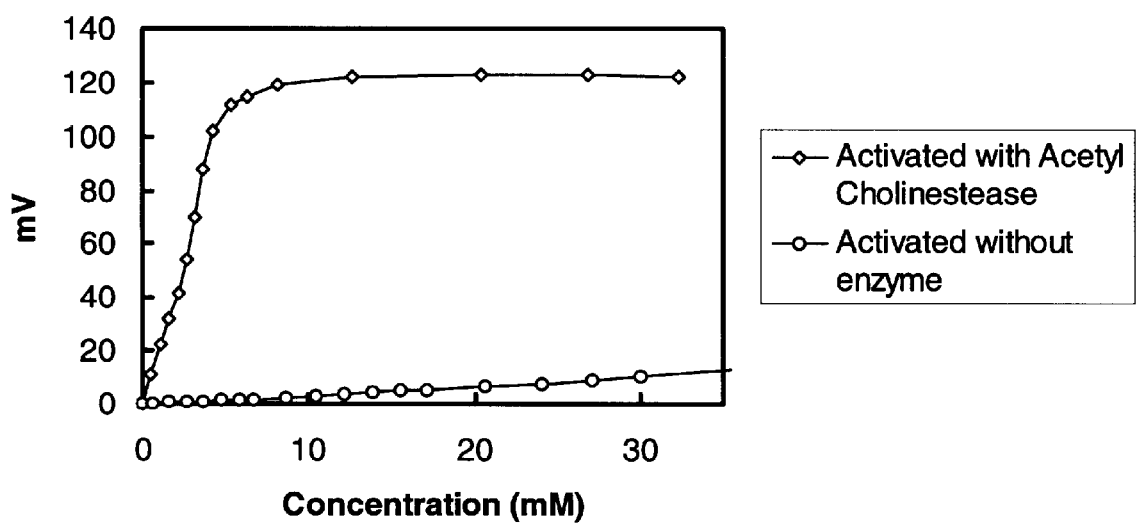
FIG. 5 shows the potentiometric response of an Ir oxide/acetylcholinesterase composite electrode and a blank Ir oxide electrode to additions of acetylcholine.

Acetylcholinesterase potentiometric electrode for determining acetylcholine. A thin film composite acetylcholine sensor was made by activating a 1 cm$^2$ Ir film in 1000 U/ml ACHE. The Ir film was prepared by dc magnetron sputtering onto a glass microscope slide with an intermediate Ti adhesion layer. An unbuffered or weakly buffered electrolyte was used to maximize the pH change at the electrode. FIG. 5 shows the potentiometric response of the composite electrode to additions of acetylcholine to unbuffered saline. A positive change in potential was observed which varied with acetylcholine concentration. The positive response indicates that acidic products are being formed at the electrode surface, in agreement with the formation of acetic acid by the enzymatic hydrolysis of acetylcholine. The shape of the calibration curve (FIG. 5) in dicates that Michaels-Menton kinetics are followed. The largest response is achieved in unbuffered media (e.g., 0.1M NaCl versus 0.1M PBS) or in low buffer concentrations (e.g., 2.5–5 mM HEPES buffer).

Figure 6:
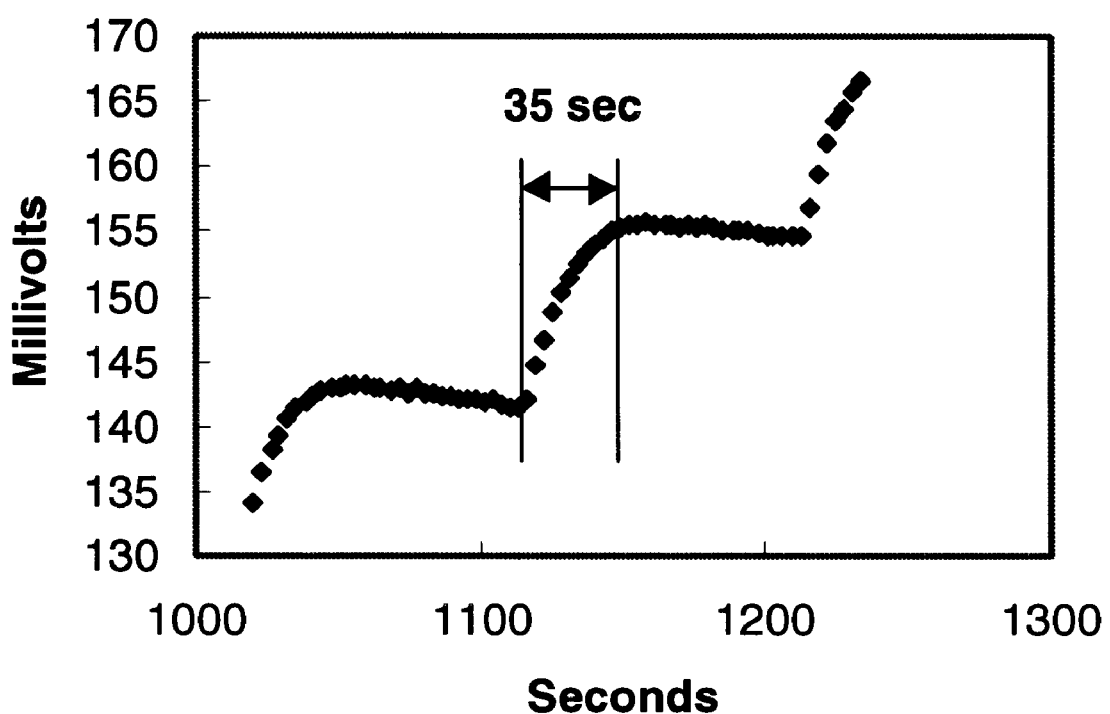
FIG. 6 shows the rate of potentiometric response of an Ir oxide/acetylcholinesterase composite electrode to addition of 1 mM acetylcholine in 0.1 M NaCl.

FIG. 6 shows the rate of response on addition of a 1 mM increment of acetylcholine during the measurement sequence to generate FIG. 5. It is seen that the full scale response in about 35 seconds. Note that this is very short compared to similar experiments reported by Tran-Minh et al. (Biosensors & Bioelectronics 5:461–471) for Ir oxide electrodes coated with polymer layers containing acetylcholinesterase (5–8 minutes).

EXAMPLE 4

Electrode for cholinesterase inhibitors. To evaluate the AChE electrode response to cholinesterase inhibitors, a 1 cm by 0.125 mm Ir wire electrode was activated 1000 U/ml AChE/0.1M PBS. The charge capacity following activation was 34 mC/cm$^2$. The electrode was then rinsed with distilled, deionized water and introduced into an electrochemical cell equipped with a magnetic stirrer, 2.5 mM HEPES buffer (pH 7.8) and a pH electrode.

Figure 7:
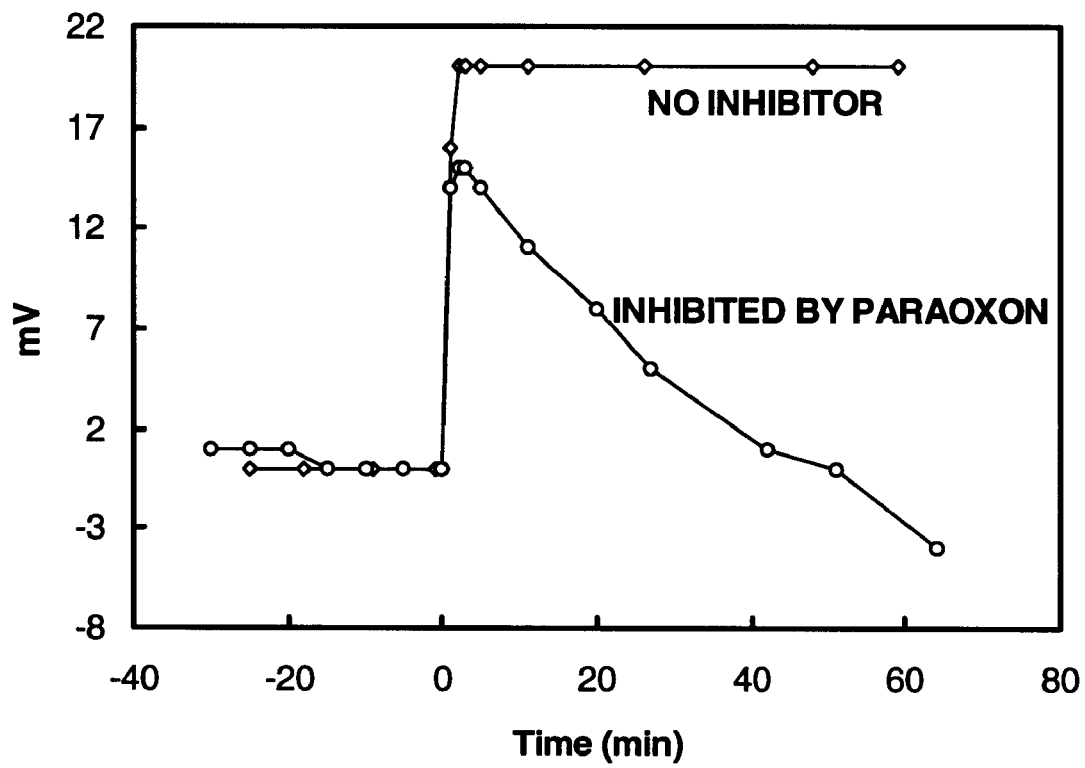
FIG. 7 shows the Ir oxide/acetylcholinesterase composite electrode potentiometric response to 5 mM acetylcholine in 2.5 mM HEPES buffer with and without $10^{-6}$ M Paraoxon inhibitor.

Acetylcholine was then added to produce a final concentration of 5 mM. As seen in FIG. 7, a potential response due to the production of acetic acid from the reaction of the electrode-bound enzyme with the solution is observed. The potential response is complete within seconds compared to minutes for Ir oxide pH electrodes coated with enzyme-bound polymer layers of prior art, as also seen in FIG. 6. This is a result of the intimate contact between the product-generating enzyme and the pH sensitive electrode matrix.

The electrodes were then rinsed in distilled water and incubated for 12 hours in a 10$^{-6}$ M paraoxon inhibitor solution in 2.5 mM HEPES buffer. The incubated electrodes were then retested for response to 5 mM acetylcholine. It is seen from FIG. 7 that an instantaneous response is observed, but on mixing the response is suppressed. The total pH change in solution was negligible. Then 10$^{-3}$ M pyridine 2-aldoxime methiodide (PAM) antidote was added to the solution. The pH of the solution was observed to drop by ~0.2 units over a period of 2 hours, indicating a partial reactivation of the electrode.

Further modifications or alterations to the invention will be apparent to those skilled in the art; the particular forms of the invention described are to be taken as preferred embodiments. The scope of the invention should be determined solely by the appended claims.

What I claim is:

1. An electrode useful in chemical sensing comprising:
   (a) an electrically conductive base material
   (b) a thin film of a porous hydrous metal oxide conductive of both electrons and ions coated thereon and
   (c) one or more substances disposed within said metal oxide, said substances possessing reactive recognition properties for one or more chemicals
   wherein the hydrous metal oxide provides electrical contact between the electrically conductive base material and a product of said reactive recognition
   said hydrous metal oxide being derived substantially from Ir, Ru, Pd, Pt, Zr, Ti and Rh, or mixtures thereof.

2. The electrode of claim 1 wherein said base material is Ir.

3. The electrode of claim 1 wherein said substances with reactive recognition properties interact with a chemical to produce a product that is electrochemically active between −0.6V and 0.8V versus an Ag/AgCl reference electrode.

4. The electrode of claim 1 obtained by electrochemical growth of the hydrous metal oxide on the parent metal in an electrolyte also containing said substances with reactive recognition properties.

5. The electrode of claim 1 obtained by electrochemical polarization of said hydrous metal oxide film in the presence of said substances with molecular recognition properties.

6. The electrode of claim 1 wherein said substance is an enzyme.

7. The electrode of claim 6 wherein the enzyme is an oxidoreductase enzyme.

8. The electrode of claim 7 wherein said oxidoreductase enzyme is glucose oxidase.

9. An amperometric biosensor having an electrode as recited in claim 1 incorporated into an electrochemical cell containing an electrolyte also containing the chemical to be sensed
   the products of said reactive recognition being detected and quantified by transferring electrons between said product and said hydrous metal oxide electrode and to an external circuit incorporating a current measuring means.

10. The amperometric biosensor of claim 9 wherein the current is greater than 10 microamps per cm$^2$ of electrode area.

11. The amperometric biosensor of claim 9 wherein said substance with reactive recognition properties is glucose oxidase, said chemical is glucose, and said products are gluconolactone and FADH$_2$ contained within the glucose oxidase
    said detection proceeding by direct electrochemical oxidation of FADH$_2$.

12. The amperometric biosensor of claim 9 wherein said substance with reactive recognition properties is glucose oxidase, said chemicals are glucose and O$_2$, and said products are gluconolactone and H$_2$O$_2$
    said detection proceeding by electrochemical oxidation of H$_2$O$_2$.

13. The amperometric biosensor of claim 9 wherein an inhibitor of said substance with reactive recognition properties is detected by a decrease in current response to the products of said reactive recognition.

14. A potentiometric biosensor having an electrode as recited in claim 1 incorporated in an electrochemical cell containing an electrolyte also containing the chemical to be sensed the products of said reactive recognition being detected by transferring protons or hydroxide to or from said hydrous metal oxide the accompanying change in the potential of the hydrous metal oxide electrode being detected by an external circuit incorporating a voltage measuring means.

15. The potentiometric biosensor of claim 14 wherein the potential changes in less than 1 minute in response to a change in chemical composition of 100 mM.

16. The potentiometric biosensor of claim 14 wherein said substance with reactive recognition properties is acetylcholinesterase, said chemical is acetylcholine, and said products include acetic acid which protonates said hydrous metal oxide.

17. The potentiometric biosensor of claim 14 wherein an inhibitor of said substance with reactive recognition properties is detected by a decrease in voltage response to the products of said reactive recognition.

18. The potentiometric biosensor of claim 14 wherein said substance with reactive recognition properties is acetylcholine, said chemical is acetylcholinesterase, and said products include acetic acid which protonates said hydrous metal oxide.

19. The electrode of claim 1 wherein at least one of said substances with molecular recognition properties is an antibody.

20. The electrode of claim 1 wherein at least one of said substances with molecular recognition properties is a nucleic acid strand.

21. The electrode of claim 1 further containing an electron transfer mediator disposed within said hydrous metal oxide.

22. The electrode of claim 21 wherein said electron transfer mediator is ferrocene or a ferrocene derivative.

23. The electrode of claim 1 wherein said substances with reactive recognition properties are acetylcholinesterase and choline oxidase.

24. An amperometric biosensor for acetylcholine comprising the electrode of claim 23 incorporated into an electrochemical cell the choline product of the said reactive recognition between acetylcholine and acetylcholinesterase interacting with choline oxidase to form betaine and a reduced product said detection proceeding by electrochemical oxidation of the reduced product.

* * * * *